United States Patent
Takahama et al.

(12)

(10) Patent No.: US 6,379,886 B1
(45) Date of Patent: *Apr. 30, 2002

(54) DIAGNOSTIC REGEANT FOR HEPATITIS C VIRUS INFECTION

(75) Inventors: Yoichi Takahama; Junichi Shiraishi, both of Hyogo-ken (JP)

(73) Assignee: TOA Medical Electronics Co., Ltd., Hyogo-ken (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/850,328

(22) Filed: May 2, 1997

(30) Foreign Application Priority Data

May 7, 1996 (JP) .............................. 8-112442

(51) Int. Cl.⁷ ............................ A61K 39/29; C12Q 1/70
(52) U.S. Cl. ........................... 435/5; 435/7.1; 435/7.92; 435/948; 436/501; 436/543; 436/811; 436/820; 424/184.1; 424/185.1; 424/186.1; 424/189.1; 424/193.1; 424/196.11; 424/204.1; 424/228.1; 530/300; 530/350; 530/403; 530/806; 530/810; 530/826
(58) Field of Search ....................... 435/5, 7.1, 7.92, 435/948; 424/184.31, 185.1, 186.1, 189.1, 193.1, 196.11, 204.1, 228.1; 436/501, 543, 811, 820; 530/300, 350, 403, 806, 810, 826

(56) References Cited

U.S. PATENT DOCUMENTS 5,164,299 A * 11/1992 Lambert .................... 435/7.92
5,436,126 A * 7/1995 Wang .......................... 435/5
5,683,864 A * 11/1997 Houghton et al. ............. 435/5
5,736,321 A * 4/1998 Hosein et al. ................. 435/5
5,747,239 A * 5/1998 Wang et al. .................... 435/5

FOREIGN PATENT DOCUMENTS

| EP | 0 318 216 A1 | * | 5/1989 |
| EP | 0442394 A | | 8/1991 |
| EP | 0468527 A | | 1/1992 |
| JP | 5-508219 | | 11/1993 |
| JP | 5-508219/93 | * | 11/1993 |
| JP | 6-102273 | | 4/1994 |
| JP | 7-198723 | * | 8/1995 |
| WO | WO90/11089 | | 10/1990 |
| WO | 91/15771 | * | 10/1991 |

OTHER PUBLICATIONS

Barrera et al. Vox. Sang. 68: 15–18, 1995.*
Patent Abstracts of Japan, vol. 095, No. 004, May 31, 1995 and JP 07 020129 A (Tokuama Soda co. Ltd), Jan. 24, 1995.
Patent Abstracts of Japan, vol. 095, No. 011, Dec. 26, 1995 and JP 07 198723 A (Nippon Zeon Co. Ltd.), Aug. 1, 1995.

* cited by examiner

*Primary Examiner*—Mary K. Zeman
(74) *Attorney, Agent, or Firm*—Morrison & Foerster LLP; Bruce Grant

(57) ABSTRACT

A diagnostic reagent for hepatitis C virus infection obtained by sensitizing a solid phase with HCV antigen and a conjugated antigen prepared by chemical bonding of HCV antigen and a carrier protein, and a method of diagnosing hepatitis C virus infection, which comprises adding the diagnostic reagent for hepatitis C virus infection to a sample, and measuring the degree of agglutination of carrier particles as the solid phase. The diagnostic reagent and the method of diagnosis enable many samples to be measured with higher sensitivity and rapidity.

11 Claims, No Drawings

DIAGNOSTIC REGEANT FOR HEPATITIS C VIRUS INFECTION

BACKGROUND OF THE INVENTION

The present invention relates to a diagnostic reagent for detecting hepatitis C virus (HCV) infection by utilizing immunoagglutination.

In regard to hepatitis C, HCV gene was detected by the research group of Chiron Corporation, U.S.A., in 1988 prior to the detection of HCV. To detect antibodies to HCV, various recombinant antigens or synthetic peptides have been investigated, and kits for detecting HCV-associated antibodies have been developed. The methods of detection now available are agar diffusion, counterimmunoelectrophoresis, radioimmunoassay, enzyme immunoassay, passive hemagglutination, and latex agglutination.

Known HCV antigen proteins for use in the detection of HCV-associated antibodies are core and envelope proteins as structural region proteins, and NS1 to NS5 proteins as non-structural region proteins. One HCV antigen protein alone is not sufficiently high in detection sensitivity, and is also problematical in specificity. Thus, a suitable combination of proteins in structural and non-structural regions is used (Proc. Natl. Acad. Sci. USA 89:10011–10015, 1992). Attempts to increase the detection sensitivity further are also made. With the particle agglutination method, for example, the number of HCV antigens for sensitization of particles is increased, or polypeptide having HCV antigenic activity is heat-treated (Japanese Laid-Open Patent Publication No. 1002273/94); alternatively, a fusion protein constructed from HCV antigen protein and carrier protein is coated onto hydrophilic particles for their sensitization (Japanese Laid-Open Patent Publication No. 198723/95).

The use of synthetic peptide as an antigen has also been attempted, but this use is generally said to lower the detection sensitivity.

Thus, there is a growing demand for a diagnostic reagent and a method of diagnosis which enable many samples to be measured with high sensitivity and rapidity.

SUMMARY OF THE INVENTION

We have conducted intensive studies in an attempt to attain such objectives. As a result, we have found that high sensitivity can be realized by chemically bonding the core antigen, NS3 antigen, NS4 antigen or NS5 antigen of HCV to carrier protein by the glutaraldehyde method to form conjugated antigens, and sensitizing carrier particles with these conjugated antigens. The use of these conjugated antigens has also markedly improved the stability of the particles.

The present invention provides a diagnostic reagent for hepatitis C virus infection obtained by sensitizing a solid phase with HCV antigen and a conjugated antigen prepared by chemical bonding of HCV antigen and a carrier protein.

The carrier protein may be any water-soluble protein, preferably the one with a molecular weight of 10,000 to 1,000,000, more preferably with a molecular weight of 30,000 to 150,000. Preferred examples are bovine serum albumin (BSA), ovalbumin, and hemocyanin. In addition, water-soluble synthetic polymers, such as polyvinyl alcohol and dextran, are also usable.

The solid phase may be carrier particles, a microtiter plate, or a test tube, but carrier particles are preferred. As the carrier particles, known particles generally used in a diagnostic reagent involving the particle agglutination method can be used. Examples include hydrophobic particles such as polystyrene latex, copolymer latex particles having a hydrophilic group such as an amino or carboxyl group on the surface of the particles, erythrocytes, and gelatin particles. More preferable is polystyrene latex.

The HCV antigen protein used in the diagnostic reagent of the present invention is the known structural region protein or non-structural region protein of HCV. The structural region protein may be core protein, while the non-structural region protein may be NS3 protein, NS4 protein or NS5 protein. The amino acid and nucleotide sequences of these antigenic proteins are described in the literature (Officially Published Patent Gazette No. 508219/93)(SEQ ID NO. 6). Where the antigenic protein results from does not matter, so long as it has HCV antigenic activity. Natural isolates, chemical synthetics, and genetic recombination products can be used. Of the proteins in these regions, a peptide of varying length can be used as the antigenic protein. Preferably, a peptide composed of 8 or more amino acids containing at least one epitope is used. More preferably, a synthetic peptide having a molecular weight of 1,000 to 5,000 is used. The peptide can be synthesized by a known method in the art, such as solid phase synthesis, fragment condensation, or classical solution synthesis. Preferably, it can be produced by the solid phase peptide synthesis method described in the literature (Merrifield, J. Am. Chem. Soc. 85:2149, 1963). According to the present invention, one or more of core, NS3, NS4 and NS5 antigen proteins containing one or more different epitopes are combined, and can be used directly, or after conjugation to a carrier protein, to sensitize carrier particles. In the Examples to be described later on, a peptide containing the 49th to 68th (SEQ ID NO. 6) amino acids in the core region described in Officially Published Patent Gazette No. 508219/93 is used as the core antigen, a peptide containing the 1706th to 1725th (SEQ ID NO. 8), 1718th to 1737th (SEQ ID NO. 9), and 1724th to 1743rd (SEQ ID NO. 10) amino acids in the NS4 region described in Officially Published Patent Gazette No. 508219/93 is used as the NS4 peptide, a peptide containing the 2287th to 2306th (SEQ ID NO. 11), 2299th to 2318th (SEQ ID NO. 12), and 2311th to 2330th (SEQ ID NO. 13) amino acids in the NS5 region described in Officially Published Patent Gazette No. 508219/93 is used as the NS5 peptide, and a peptide containing the 1192nd to 1457th (SEQ ID NO. 7) amino acids in the NS3 region described in Officially Published Patent Gazette No. 508219/93 is used as the NS3 peptide. However, the antigenic proteins of the present invention are not restricted to these peptides.

Each of the above-described antigenic proteins is chemically bonded to the carrier protein to prepare a conjugated antigen. The antigenic protein has been found to show higher detection sensitivity when sensitizing the carrier particles as a conjugated antigen than when sensitizing them directly. For the antigen protein with a molecular weight of 10,000 or more like the NS3 antigen used in the present invention, however, no marked difference in the sensitivity has been observed. Thus, it is permissible to sensitize the carrier particles directly with such a high molecular weight antigen protein, and sensitize the particles with the other antigen proteins as conjugated antigens. Bonding of the carrier protein and the antigen protein can be performed by a known method using carbodiimide, periodic acid, maleimide or glutaraldehyde. The use of the glutaraldehyde method is preferred, because their bonding by glutaraldehyde-induced crosslinking increases reactivity. For the preparation of the conjugated antigen, the carrier protein and the antigen protein are mixed at a ratio, as the ratio of the numbers of molecules for the two, of about 1:3 to 1:20, preferably about 1:4 to 1:9, more preferably about 1:6 to 1:8. The so prepared conjugated antigen is bound to(or caused to sensitize) carrier particles by a known method, which may be, say, physical adsorption or chemical adsorption. As described previously, the NS3 antigen may be directly caused to sensitize carrier particles without forming a conjugated antigen together with the carrier protein. This can be performed by the same method as described above. Sensitization is carried out in a buffer, a solution with a buffer action, such as phosphate buffer, glycine buffer, TRIS buffer or acetate buffer, preferably at a pH of 3 to 8, more preferably at pH 4 to 5.

The present invention also provides a method of diagnosing hepatitis C virus infection, which comprises adding the aforementioned diagnostic reagent for hepatitis C virus infection to a sample, and measuring the degree of agglutination of the carrier particles by a flow cytometer. The diagnostic reagent for hepatitis C virus infection according to the present invention also reacts with anti-HCV antibodies, if present in the sample, to cause agglutination. The resulting agglutination may be measured visually or by turbidity or absorbance. However, a rapid, high-sensitivity, high-precision/accuracy measurement can be made by optically measuring the agglutinated particles with a full-automatic immunoagglutination measuring system (e.g., PAMIA-30™, TOA MEDICAL ELECTRONICS Co., Ltd) which relies on the principle of a flow cytometer. In detail, the sample is guided into a flow cell, arranged in a row, and passed by a sheath flow mechanism. A laser beam is projected onto it, and the intensity of scattered light produced is measured to tell the degree of agglutination. The number of the agglutinated particles (P: Polymer) and the number of non-agglutinated particles (M: Monomer) are counted. From the P and M, P/T (T=P+M) is calculated, and the presence or absence of anti-HCV antibodies is qualitatively evaluated based on the cutoff value obtained beforehand. This method enables anti-HCV antibodies to be detected with high sensitivity. A suitable particle size of the particles would make measurement possible by a blood analyzer or a particle size analyzer using electrical resistance. However, measurement by an optical method is preferred to avoid a problem such as clogging of the detector.

PREFERRED EMBODIMENTS OF THE INVENTION

The use of the diagnostic reagent for hepatitis C virus infection according to the present invention permits highly sensitive, early diagnosis of infection with hepatitis C virus as compared with commercially available diagnostic reagents. Actually, the diagnostic reagent of the present invention was tested using panel serum composed of several samples taken over time from the same individual in the course of seroconversion of anti-HCV antibodies (e.g., HCV Seroconversion Panel, imported and distributed by Kyowa Medics Co., Ltd, manufactured by BOSTON BIOMEDICA, INC.). The diagnostic reagent for hepatitis C virus infection of the present invention was demonstrated to detect HCV infection in an earlier stage than conventional methods, passive hemagglutination (PHA) using erythrocytes, enzyme immunoassay (EIA) and enzyme-linked immunosorbent assay (ELISA), namely, in the initial stage of infection.

The diagnostic reagent of the present invention was also compared with a diagnostic reagent produced by using the same antigen as in the inventive diagnostic reagent, but directly causing this antigen to sensitize carrier particles without preparing its conjugated antigen together with a carrier protein. The diagnostic reagent of the present invention was found to be superior in the detection sensitivity.

Furthermore, the diagnostic reagent of the present invention does not decrease in the detection sensitivity even after long-term storage. Thus, it proves a stable diagnostic reagent.

The diagnostic method of the present invention, compared with a conventional method such as ELISA, does not involve a complicated washing step, but can be performed by a mere step of mixing the inventive diagnostic reagent for HCV infection (preferably, latex particles sensitized with HCV antigen) with a sample (preferably, a subject's blood). The diagnostic method of the present invention also enables measurement by a measuring system which performs both of the above mixing step and the measuring step full-automatically. Thus, this method is suitable for measuring many samples.

The present invention will be described in greater detail by reference to Examples, which do not limit the scope of the invention.

EXAMPLE 1

Preparation of HCV Conjugated Antigens

For use as HCV antigen, NS3 antigen was produced by genetic recombination based on the description of Example 1 of Officially Published Patent Gazette No. 508219/93. The NS3 antigen was used the 1192nd to 1457th (SEQ ID NO. 7) amino acids of HCV protein.

As core antigen, NS4 antigen and NS5 antigen, peptides containing amino acid sequences composed of the 49th to 68th (SEQ ID NO. 6), the 1706th to 1725th (SEQ ID NO. 8), and the 2287th to 2306th (SEQ ID NO. 11) amino acids, respectively, described in Officially Published Patent Gazette No. 508219/93 were synthesized by the peptide synthesizer Model 431A (PERKIN ELMER).

Seven volumes of a 0.1% (w/v) solution of core antigen (a peptide of the 49th to 68th amino acids) in 10 mM PBS, pH 7.0, was added to one volume of a 0.1% (w/v) solution of BSA (a commercially available product with a molecular weight of 66,000) in 10 mM PBS, pH 7.0. To the mixture, 10 mM PBS, pH 7.0, was further added to make 9 volumes. Then, a 1% aqueous solution of glutaraldehyde was added to initiate the reaction at a reaction temperature of 30° C. Thirty minutes later, one volume of a 20% aqueous solution of glycine was added to terminate the reaction.

A similar procedure was applied to NS3, NS4 and NS5 antigens as well. That is, 1 to 8 volumes of a 0.1% (w/v) solution of the HCV antigen in 10 mM PBS, pH 6 to 8, was reacted with 1 volume of a 1% (w/v) solution of BSA in 10 mM PBS, pH 6 to 8, to prepare HCV conjugated antigens.

EXAMPLE 2

Production of HCV Antigen-sensitized Latex

To a 5% (w/v) dispersion of polystyrene latex particles (Sekisui Chemical Co., Ltd) with a particle diameter of 0.78

μm in 10 mM PBS, pH 4.0, the NS3 conjugated antigen, the NS4 conjugated antigen and the NS5 conjugated antigen prepared in Example 1 was added in an amount of 50 μg each per ml of the latex dispersion. The mixture was reacted for 24 hours at 4° C. Then, the reaction mixture was centrifuged for 10 min at 12,000 rpm, and 0.1M PBS, pH 7.0, containing 1 mg/ml BSA was added to the same concentration as initially added, to disperse the particles. The dispersion was centrifuged again, and dispersed in the same buffer of the same concentration to produce HCV antigen-sensitized latex.

EXAMPLE 3

Agglutination Reaction

To 10 μl of a sample (a subject's blood), 10 μl of the HCV antigen-sensitized latex (5%) prepared in Example 2 was added, and 80 μl of 0.1M phosphate buffer containing 1 mg/ml BSA was further added. After the mixture was reacted for 15 min at 45° C., the degree of agglutination of the latex particles was measured based on forward-scattered light by means of a full-automatic immunoagglutination measuring system (PAMIA-30™, TOA MEDICAL ELECTRONICS Co., Ltd).

The degree of agglutination is expressed as the percentage of the number of the agglutinated particles to the total number of the particles (P/T, %).

The results of the measurements are presented in Table 1. As shown in Table 1, a sufficient degree of agglutination was obtained with HCV antibody-positive samples, while no agglutination of latex occurred with HCV antibody-negative samples. Since agglutination was thus observed in samples containing HCV antibodies, one sees that agglutination took place upon the reaction of the HCV antigen-sensitized latex particles with HCV antibodies.

TABLE 1

Degree of agglutination (P/T, %)

| HCV antibody-positive samples | | | | | HCV antibody-negative samples | | | | |
|---|---|---|---|---|---|---|---|---|---|
| A | B | C | D | E | F | G | H | I | J |
| 72.52 | 54.56 | 44.89 | 43.02 | 73.00 | 0.95 | 0.90 | 0.82 | 0.82 | 0.92 |

Cutoff value: 2.79%

EXAMPLE 4

Detection Sensitivity at Early Stage

The detection sensitivity for HCV antibody seroconversion was tested using the commercially available HCV Seroconversion Panels PHV901, PHV902 and PHV903 (importer and distributor: Kyowa Medics Co., Ltd, manufacturer: BOSTON BIOMEDICA, INC.) that are composed of several samples taken over time from the same individuals in the course of seroconversion of HCV antibodies. Counting immunoassay (CIA) of the present invention using the diagnostic reagent prepared in Example 2 was compared with the following methods using the products of other companies:

Company A: Passive hemagglutination (PHA) using erythrocytes HCV antigens used: Core, NS3, NS4

Company B: Enzyme immunoassay (EIA) HCV antigens used: Core, NS3, NS4

Company C: Enzyme-linked immunosorbent assay (ELISA) HCV antigens used: Core, NS3, NS4

The results obtained are shown in Tables 2, 3 and 4 (the data of Company B's and Company C's products in the tables are the values indicated on the labels attached to the panels). When the diagnostic reagent and the diagnostic method of the present invention were used, HCV infection in Panels PHV902 and PHV903 (the subjects, the presenters of these panels, tested positive for antibodies in PCR from the first day of blood sampling) was detected earlier than the use of the other companies' products.

TABLE 2

HCV Seroconversion Panel PHV901

| | | | Measured value | | | Labeled value | | | |
|---|---|---|---|---|---|---|---|---|---|
| | | | Present invention CIA | | Company A PHA | Company B EIA II | | Company C ELISA II | |
| ID | Day of sampling | Number of days | Evaluation | P/T | Evaluation | Evaluation | COI* | Evaluation | COI* |
| PHV901-01 | 93/09/23 | 0 | − | 1.0 | − | − | 0.2 | − | 0.0 |
| PHV901-02 | 93/11/27 | 72 | − | 1.1 | − | − | 0.2 | − | 0.0 |
| PHV901-03 | 93/12/29 | 104 | + | 73.3 | + | + | 1.6 | + | 1.2 |
| PHV901-04 | 93/21/31 | 106 | + | 74.6 | + | + | 1.7 | + | 1.2 |
| PHV901-05 | 94/01/05 | 111 | + | 75.3 | + | + | 1.7 | + | 1.4 |
| PHV901-06 | 94/01/07 | 113 | + | 73.8 | + | + | 1.6 | + | 1.8 |
| PHV901-07 | 94/02/01 | 138 | + | 73.8 | + | + | 3.8 | + | >4 |
| PHV901-08 | 94/02/09 | 146 | + | 71.5 | + | + | 3.6 | + | >4 |
| PHV901-09 | 93/03/01 | 166 | + | 67.0 | + | + | >5 | + | >4 |
| PHV901-10 | 94/03/08 | 173 | + | 63.9 | + | + | >5 | + | >4 |
| PHV901-11 | 94/04/14 | 209 | + | 61.7 | + | + | >5 | + | >4 |

Cutoff: 1.75%

COI* = Cutoff index

TABLE 3

HCV Seroconversion Panel PHV902

| | | | Measured value | | | Labeled value | | | |
| | | | Present invention CIA | | Company A PHA | Company B EIA II | | Company C ELISA II | | |
| ID | Day of sampling | Number of days | Evaluation | P/T | Evaluation | Evaluation | COI* | Evaluation | COI* | PCR |
|---|---|---|---|---|---|---|---|---|---|---|
| PHV902-01 | 92/02/07 | 0  | − | 1.0  | − | − | 0.2 | − | 0.2 | + |
| PHV902-02 | 92/02/12 | 2  | − | 1.0  | − | − | 0.2 | − | 0.2 | + |
| PHV902-03 | 92/02/17 | 7  | + | 3.0  | − | − | 0.4 | − | 0.3 | + |
| PHV902-04 | 92/02/19 | 9  | + | 4.4  | + | − | 0.8 | − | 0.5 | + |
| PHV902-05 | 92/02/24 | 14 | + | 17.0 | + | + | 3.9 | + | >4  | + |
| PHV902-06 | 92/02/26 | 16 | + | 18.0 | + | + | 5.0 | + | >4  | + |
| PHV902-07 | 92/03/02 | 21 | + | 17.6 | + | + | >5  | + | >4  | + |

Cutoff: 1.75%

COI* = Cutoff index

TABLE 4

HCV Seroconversion Panel PHV903

| | | | Measured value | | | Labeled value | | | |
| | | | Present invention CIA | | Company A PHA | Company B EIA II | | Company C ELISA II | | |
| ID | Day of sampling | Number of days | Evaluation | P/T | Evaluation | Evaluation | COI* | Evaluation | COI* | PCR |
|---|---|---|---|---|---|---|---|---|---|---|
| PHV903-01 | 92/02/07 | 0  | − | 0.8  | − | − | 0.2 | − | 0.2 | + |
| PHV903-02 | 92/02/12 | 5  | + | 2.2  | − | − | 0.4 | − | 0.6 | + |
| PHV903-03 | 92/02/14 | 7  | + | 4.2  | − | − | 0.5 | − | 0.7 | + |
| PHV903-04 | 92/02/19 | 12 | + | 12.9 | + | − | 0.8 | + | 1.5 | + |
| PHV903-05 | 92/02/21 | 14 | + | 11.5 | + | − | 0.7 | + | 1.5 | + |
| PHV903-06 | 92/02/26 | 19 | + | 28.2 | + | + | 1.7 | + | 4.0 | + |
| PHV903-07 | 92/02/28 | 21 | + | 29.1 | + | + | 1.9 | + | >4  | + |
| PHV903-08 | 92/03/04 | 26 | + | 26.6 | + | + | 2.3 | + | >4  | + |

Cutoff: 1.75%

COI* = Cutoff index

Table 5 Comparison with Diagnostic Reagent Prepared by Direct Sensitization with HCV Antigen The diagnostic reagent of the present invention and a diagnostic reagent prepared by direct sensitization with the same HCV antigen as in the inventive diagnostic reagent were tested for sensitivity for detection of HCV antibodies. NS3 antigen (obtained by genetic recombination), core antigen (peptide obtained by synthesis), NS4 antigen (peptide obtained by synthesis) and NS5 antigen (peptide obtained by synthesis) were converted into conjugated antigens together with BSA, and used for sensitization in the same manner as in Example 2. Thus, HCV conjugated antigen-sensitized latex was produced.

As a control, HCV antigen-directly-sensitized latex was produced by direct sensitization using the same antigens and the same conditions for sensitization.

Using these latices, the degree of agglutination (P/T, %) of HCV antibody-positive samples (A to E) and that of HCV antibody-negative samples (F to J) were measured by the method of Example 3. Whether each sample was positive or negative for HCV antibodies was evaluated in view of the cutoff value (1.95% for the conjugated antigen-sensitized latex; 1.01% for the antigen-directly-sensitized latex). The results are shown in Table 5.

TABLE 5

| | Conjugated antigen-sensitized latex | | Antigen-directly-sensitized latex | |
|---|---|---|---|---|
| Sample | Degree of agglutination (%) | Evaluation | Degree of agglutination (%) | Evaluation |
| A | 15.87 | Positive | 0.34  | Negative |
| B | 66.28 | Positive | 24.36 | Positive |
| C | 35.28 | Positive | 6.35  | Positive |
| D | 50.98 | Positive | 15.56 | Positive |
| E | 17.88 | Positive | 0.55  | Negative |
| F | 0.46  | Negative | 0.34 | Negative |
| G | 0.56  | Negative | 0.36 | Negative |
| H | 0.79  | Negative | 0.35 | Negative |

TABLE 5-continued

| | Conjugated antigen-sensitized latex | | Antigen-directly-sensitized latex | |
|---|---|---|---|---|
| Sample | Degree of agglutination (%) | Evaluation | Degree of agglutination (%) | Evaluation |
| I | 0.62 | Negative | 0.56 | Negative |
| J | 0.65 | Negative | 0.55 | Negative |

In the HCV antibody-positive samples A and E, HCV antibodies were not detected with the diagnostic reagents involving direct sensitization with the antigens, but were detected with the diagnostic reagent of the present invention involving sensitization with the conjugated antigens.

EXAMPLE 6

Test for Long-term Storage Stability

The 5% (w/v) suspensions of HCV antigen-sensitized latices in 0.1M PBS, pH 7.0, in Example 5 were stored in a refrigerated condition to examine the storage stability of the diagnostic reagents. The results are shown in Table 6.

TABLE 6

| | HCV antibody-negative pooled serum | | HCV antibody-positive pooled serum | | Cutoff value | |
|---|---|---|---|---|---|---|
| | Conjugated antigen-sensitized | Directly sensitized | Conjugated antigen-sensitized | Directly sensitized | Conjugated antigen-sensitized | Directly sensitized |
| 0 month | 0.71% | 0.75% | 41.90% | 12.46% | 2.35% | 1.25% |
| 1 month | 0.71% | 0.72% | 40.85% | 11.56% | 2.51% | 1.35% |
| 3 months | 0.75% | 1.02% | 46.83% | 10.79% | 2.56% | 1.56% |
| 6 months | 0.78% | 1.22% | 43.47% | 10.62% | 2.55% | 1.82% |
| 9 months | 0.82% | 1.50% | 43.86% | 9.79% | 2.25% | 2.10% |
| 12 months | 0.75% | 1.62% | 41.62% | 8.62% | 2.33% | 2.32% |
| 13 months | 0.78% | 1.97% | 43.35% | 8.65% | 2.44% | 2.57% |

The above results demonstrate that the conjugated antigen-sensitized latex was stable in terms of the degree of agglutination even when stored for a long period of 13 months. In the case of the directly sensitized latex, on the other hand, the test using HCV antibody-negative pooled serum showed gradual increases in the degree of agglutination during long-term storage, while the test using HCV antibody-positive pooled serum showed gradual decreases in the degree of agglutination. Gradual increases in the cutoff value were also observed with the directly sensitized latex.

EXAMPLE 7

Production (2) of HCV Antigen-sensitized Latex

HCV antigen-sensitized latex was prepared by the same procedure as in Example 2 with the use of the same HCV antigens as in Example 1, except that NS3 antigen was not formed into conjugated antigen, but was used for direct sensitization.

EXAMPLE 8

Production (3) of HCV Antigen-sensitized Latex

The same NS3 antigen as in Example 1 was used. Core antigen was a peptide of the 49th to 68th (SEQ ID NO. 6) amino acids described in the aforementioned publication (Officially Published Patent Gazette No. 508219/93). NS4 antigen was peptides of the 1706th to 1725th (SEQ ID NO. 8) and the 1718th (SEQ ID NO. 9) to 1737th amino acids described there. NS5 antigen was peptides of the 2287th to 2306th (SEQ ID NO. 11) and the 2299th to 2318th (SEQ ID NO. 12) amino acids described there. As in Example 1, 1 to 8 volumes of a 0.1% (w/v) HCV antigen solution was reacted with 1 volume of a 1% (w/v) BSA solution to prepare HCV conjugated antigens. Using them, HCV antigen-sensitized latex was prepared in the same manner as in Example 2.

EXAMPLE 9

Production (4) of HCV Antigen-sensitized Latex

The same NS3 antigen as in Example 1 was used. Core antigen was a peptide of the 49th to 68th (SEQ ID NO. 6) amino acids described in the aforementioned publication. NS4 antigen was peptides of the 1706th to 1725th (SEQ ID NO. 8), the 1718th to 1737th (SEQ ID NO. 9) and the 1724th to 1743rd (SEQ ID NO. 10) amino acids described there. NS5 antigen was peptides of the 2287th to 2306th (SEQ ID NO. 11), the 2299th to 2318th (SEQ ID NO. 12) and the 2311th to 2330th (SEQ ID NO. 13) amino acids described there. As in Example 1, 1 to 8 volumes of a 0.1% (w/v) HCV antigen solution was reacted with 1 volume of a 1% (w/v) BSA solution to prepare HCV conjugated antigens. Using them, HCV antigen-sensitized latex was prepared in the same manner as in Example 2.

What is claimed is:

1. A diagnostic reagent for detecting hepatitis C virus (HCV) infection comprising a solid phase to which three or more different HCV antigen-carrier protein conjugates are bound, wherein:
   the carrier protein and HCV antigen are present in each conjugate at a ratio of about 1:3 to 1:20 (carrier protein:hepatitis C virus antigen),
   each HCV antigen-protein conjugate has only one type of HCV antigen bound to it, and
   each HCV antigen is from an antigen selected from the group consisting of core antigen, NS3 antigen, NS4 antigen and NS5 antigen.

2. A diagnostic reagent for hepatitis C virus (HCV) infection comprising a solid phase to which three or more different HCV antigen components are bound, wherein:
   at least one of the antigen components is from an antigen selected from the group consisting of core antigen, NS4 antigen and the NS5 antigen and is attached to a carrier protein to form a HCV antigen-protein conjugate,
   the bound carrier protein and HCV antigen are present in each component at a ratio of about 1:3 to 1:20 (carrier protein:hepatitis C virus antigen),
   the HCV antigen-protein conjugate has only one type of HCV antigen bound to it, and
   each HCV antigen component is from an HCV antigen selected from the group consisting of core antigen, NS3 antigen, NS4 antigen and NS5 antigen.

3. The diagnostic reagent for hepatitis C virus infection of claim 1 or 2, wherein each of the antigens of the three or more antigen-carrier protein conjugates has one or more different epitopes having HCV antigenic activity.

4. The diagnostic reagent for hepatitis C virus infection of claim 1 or 2, wherein the carrier protein is selected from the group consisting of bovine serum albumin (BSA), ovalbumin and hemocyanin.

5. The diagnostic reagent for hepatitis C virus infection of claim 1, wherein the carrier protein is selected from the group consisting of BSA, ovalbumin and hemocyanin.

6. The diagnostic reagent for hepatitis C virus infection of claim 1 or 2 wherein the solid phase is carrier particles.

7. The diagnostic reagent for hepatitis C virus infection of claim 6, wherein the carrier particles are hydrophobic particles.

8. The diagnostic reagent for hepatitis C virus infection of claim 7, wherein the hydrophobic particles are polystyrene latex.

9. A method of diagnosing the presence or absence of hepatitis C virus infection, comprises a) contacting the diagnostic reagent for hepatitis C virus infection according to claim 1 or 2 with a sample,
b) incubating the contacted sample under agglutinating conditions, and
c) measuring the degree of agglutination of the carrier particles,
   whereby the degree of agglutination is correlated with the presence or absence of hepatitis C virus infection.

10. The method of diagnosing the presence or absence of hepatitis C virus infection of claim 9, wherein the degree of agglutination is measured by a flow cytometer.

11. The method of diagnosing the presence or absence of hepatitis C virus infection as claimed in claim 10, wherein the measurement by flow cytometry is made by measuring forward-scattered light.

\* \* \* \* \*

UNITED STATES PATENT AND TRADEMARK OFFICE
CERTIFICATE OF CORRECTION

PATENT NO.    : 6,379,886 B1
DATED         : April 30, 2002
INVENTOR(S)   : Yoichi Takahama et al.

It is certified that error appears in the above-identified patent and that said Letters Patent is hereby corrected as shown below:

<u>Title page,</u>
Item [54], Title, change "REGEANT" to -- REAGENT --
Item [73], Assignee, change "TOA Medical Electronics Co., Ltd., Hyogo-ken (JP)" to -- SYSMEX CORPORATION, Kobe-Shi Hyogo (JP) --

Signed and Sealed this

First Day of April, 2003

JAMES E. ROGAN
*Director of the United States Patent and Trademark Office*

SEQUENCE LISTING (1) GENERAL INFORMATION:

(iii) NUMBER OF SEQUENCES: 13

(2) INFORMATION FOR SEQ ID NO:1:

(i) SEQUENCE CHARACTERISTICS:
      (A) LENGTH: 3011 amino acids
      (B) TYPE: amino acid
      (C) STRANDEDNESS: single
      (D) TOPOLOGY: linear (ii) MOLECULE TYPE: peptide (xi) SEQUENCE DESCRIPTION: SEQ ID NO:1:

```
Met Ser Thr Asn Pro Lys Pro Gln Lys Lys Asn Lys Arg Asn Thr Asn
 1               5                  10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly Lys Val Ile Asp Thr Leu Thr Cys
        115                 120                 125

Gly Phe Ala Asp Leu Met Gly Tyr Ile Pro Leu Val Gly Ala Pro Leu
    130                 135                 140

Gly Gly Ala Ala Arg Ala Leu Ala His Gly Val Arg Val Leu Glu Asp
145                 150                 155                 160

Gly Val Asn Tyr Ala Thr Gly Asn Leu Pro Gly Cys Ser Phe Ser Ile
                165                 170                 175

Phe Leu Leu Ala Leu Leu Ser Cys Leu Thr Val Pro Ala Ser Ala Tyr
            180                 185                 190

Gln Val Arg Asn Ser Thr Gly Leu Tyr His Val Thr Asn Asp Cys Pro
        195                 200                 205

Asn Ser Ser Ile Val Tyr Glu Ala Ala Asp Ala Ile Leu His Thr Pro
    210                 215                 220

Gly Cys Val Pro Cys Val Arg Glu Gly Asn Ala Ser Arg Cys Trp Val
225                 230                 235                 240

Ala Met Thr Pro Thr Val Ala Thr Arg Asp Gly Lys Leu Pro Ala Thr
                245                 250                 255

Gln Leu Arg Arg His Ile Asp Leu Leu Val Gly Ser Ala Thr Leu Cys
            260                 265                 270

Ser Ala Leu Tyr Val Gly Asp Leu Cys Gly Ser Val Phe Leu Val Gly
        275                 280                 285

Gln Leu Phe Thr Phe Ser Pro Arg Arg His Trp Thr Thr Gln Gly Cys
    290                 295                 300

Asn Cys Ser Ile Tyr Pro Gly His Ile Thr Gly His Arg Met Ala Trp
305                 310                 315                 320
```

-continued

Asp Met Met Met Asn Trp Ser Pro Thr Thr Ala Leu Val Met Ala Gln
            325                 330                 335

Leu Leu Arg Ile Pro Gln Ala Ile Leu Asp Met Ile Ala Gly Ala His
            340                 345                 350

Trp Gly Val Leu Ala Gly Ile Ala Tyr Phe Ser Met Val Gly Asn Trp
            355                 360                 365

Ala Lys Val Leu Val Val Leu Leu Phe Ala Gly Val Asp Ala Glu
        370                 375                 380

Thr His Val Thr Gly Gly Ser Ala Gly His Thr Val Ser Gly Phe Val
385                 390                 395                 400

Ser Leu Leu Ala Pro Gly Ala Lys Gln Asn Val Gln Leu Ile Asn Thr
                405                 410                 415

Asn Gly Ser Trp His Leu Asn Ser Thr Ala Leu Asn Cys Asn Asp Ser
            420                 425                 430

Leu Asn Thr Gly Trp Leu Ala Gly Leu Phe Tyr His His Lys Phe Asn
            435                 440                 445

Ser Ser Gly Cys Pro Glu Arg Leu Ala Ser Cys Arg Pro Leu Thr Asp
        450                 455                 460

Phe Asp Gln Gly Trp Gly Pro Ile Ser Tyr Ala Asn Gly Ser Gly Pro
465                 470                 475                 480

Asp Gln Arg Pro Tyr Cys Trp His Tyr Pro Pro Lys Pro Cys Gly Ile
                485                 490                 495

Val Pro Ala Lys Ser Val Cys Gly Pro Val Tyr Cys Phe Thr Pro Ser
            500                 505                 510

Pro Val Val Val Gly Thr Thr Asp Arg Ser Gly Ala Pro Thr Tyr Ser
        515                 520                 525

Trp Gly Glu Asn Asp Thr Asp Val Phe Val Leu Asn Asn Thr Arg Pro
        530                 535                 540

Pro Leu Gly Asn Trp Phe Gly Cys Thr Trp Met Asn Ser Thr Gly Phe
545                 550                 555                 560

Thr Lys Val Cys Gly Ala Pro Pro Cys Val Ile Gly Gly Ala Gly Asn
            565                 570                 575

Asn Thr Leu His Cys Pro Thr Asp Cys Phe Arg Lys His Pro Asp Ala
            580                 585                 590

Thr Tyr Ser Arg Cys Gly Ser Gly Pro Trp Leu Thr Pro Arg Cys Leu
        595                 600                 605

Val Asp Tyr Pro Tyr Arg Leu Trp His Tyr Pro Cys Thr Ile Asn Tyr
        610                 615                 620

Thr Ile Phe Lys Ile Arg Met Tyr Val Gly Gly Val Glu His Arg Leu
625                 630                 635                 640

Glu Ala Ala Cys Asn Trp Thr Arg Gly Glu Arg Cys Asp Leu Glu Asp
            645                 650                 655

Arg Asp Arg Ser Glu Leu Ser Pro Leu Leu Leu Thr Thr Thr Gln Trp
            660                 665                 670

Gln Val Leu Pro Cys Ser Phe Thr Thr Leu Pro Ala Leu Ser Thr Gly
        675                 680                 685

Leu Ile His Leu His Gln Asn Ile Val Asp Val Gln Tyr Leu Tyr Gly
        690                 695                 700

Val Gly Ser Ser Ile Ala Ser Trp Ala Ile Lys Trp Glu Tyr Val Val
705                 710                 715                 720

Leu Leu Phe Leu Leu Leu Ala Asp Ala Arg Val Cys Ser Cys Leu Trp
            725                 730                 735

-continued

```
Met Met Leu Leu Ile Ser Gln Ala Glu Ala Ala Leu Glu Asn Leu Val
            740                 745                 750

Ile Leu Asn Ala Ala Ser Leu Ala Gly Thr His Gly Leu Val Ser Phe
            755                 760                 765

Leu Val Phe Phe Cys Phe Ala Trp Tyr Leu Lys Gly Lys Trp Val Pro
            770                 775                 780

Gly Ala Val Tyr Thr Phe Tyr Gly Met Trp Pro Leu Leu Leu Leu Leu
785                 790                 795                 800

Leu Ala Leu Pro Gln Arg Ala Tyr Ala Leu Asp Thr Glu Val Ala Ala
            805                 810                 815

Ser Cys Gly Gly Val Val Leu Val Gly Leu Met Ala Leu Thr Leu Ser
            820                 825                 830

Pro Tyr Tyr Lys Arg Tyr Ile Ser Trp Cys Leu Trp Trp Leu Gln Tyr
            835                 840                 845

Phe Leu Thr Arg Val Glu Ala Gln Leu His Val Trp Ile Pro Pro Leu
            850                 855                 860

Asn Val Arg Gly Gly Arg Asp Ala Val Ile Leu Leu Met Cys Ala Val
865                 870                 875                 880

His Pro Thr Leu Val Phe Asp Ile Thr Lys Leu Leu Leu Ala Val Phe
            885                 890                 895

Gly Pro Leu Trp Ile Leu Gln Ala Ser Leu Leu Lys Val Pro Tyr Phe
            900                 905                 910

Val Arg Val Gln Gly Leu Leu Arg Phe Cys Ala Leu Ala Arg Lys Met
            915                 920                 925

Ile Gly Gly His Tyr Val Gln Met Val Ile Ile Lys Leu Gly Ala Leu
            930                 935                 940

Thr Gly Thr Tyr Val Tyr Asn His Leu Thr Pro Leu Arg Asp Trp Ala
945                 950                 955                 960

His Asn Gly Leu Arg Asp Leu Ala Val Ala Val Glu Pro Val Val Phe
            965                 970                 975

Ser Gln Met Glu Thr Lys Leu Ile Thr Trp Gly Ala Asp Thr Ala Ala
            980                 985                 990

Cys Gly Asp Ile Ile Asn Gly Leu Pro Val Ser Ala Arg Arg Gly Arg
            995                 1000                1005

Glu Ile Leu Leu Gly Pro Ala Asp Gly Met Val Ser Lys Gly Trp Arg
            1010                1015                1020

Leu Leu Ala Pro Ile Thr Ala Tyr Ala Gln Gln Thr Arg Gly Leu Leu
1025                1030                1035                104

Gly Cys Ile Ile Thr Ser Leu Thr Gly Arg Asp Lys Asn Gln Val Glu
            1045                1050                1055

Gly Glu Val Gln Ile Val Ser Thr Ala Ala Gln Thr Phe Leu Ala Thr
            1060                1065                1070

Cys Ile Asn Gly Val Cys Trp Thr Val Tyr His Gly Ala Gly Thr Arg
            1075                1080                1085

Thr Ile Ala Ser Pro Lys Gly Pro Val Ile Gln Met Tyr Thr Asn Val
            1090                1095                1100

Asp Gln Asp Leu Val Gly Trp Pro Ala Pro Gln Gly Ser Arg Ser Leu
1105                1110                1115                112

Thr Pro Cys Thr Cys Gly Ser Ser Asp Leu Tyr Leu Val Thr Arg His
            1125                1130                1135

Ala Asp Val Ile Pro Val Arg Arg Arg Gly Asp Ser Arg Gly Ser Leu
            1140                1145                1150

Leu Ser Pro Arg Pro Ile Ser Tyr Leu Lys Gly Ser Ser Gly Gly Pro
```

-continued

```
            1155                1160                1165
Leu Leu Cys Pro Ala Gly His Ala Val Gly Ile Phe Arg Ala Ala Val
        1170                1175                1180
Cys Thr Arg Gly Val Ala Lys Ala Val Asp Phe Ile Pro Val Glu Asn
1185                1190                1195                120
Leu Glu Thr Thr Met Arg Ser Pro Val Phe Thr Asp Asn Ser Ser Pro
                1205                1210                1215
Pro Val Val Pro Gln Ser Phe Gln Val Ala His Leu His Ala Pro Thr
            1220                1225                1230
Gly Ser Gly Lys Ser Thr Lys Val Pro Ala Ala Tyr Ala Ala Gln Gly
        1235                1240                1245
Tyr Lys Val Leu Val Leu Asn Pro Ser Val Ala Ala Thr Leu Gly Phe
    1250                1255                1260
Gly Ala Tyr Met Ser Lys Ala His Gly Ile Asp Pro Asn Ile Arg Thr
1265                1270                1275                128
Gly Val Arg Thr Ile Thr Thr Gly Ser Pro Ile Thr Tyr Ser Thr Tyr
                1285                1290                1295
Gly Lys Phe Leu Ala Asp Gly Gly Cys Ser Gly Gly Ala Tyr Asp Ile
            1300                1305                1310
Ile Ile Cys Asp Glu Cys His Ser Thr Asp Ala Thr Ser Ile Leu Gly
        1315                1320                1325
Ile Gly Thr Val Leu Asp Gln Ala Glu Thr Ala Gly Ala Arg Leu Val
    1330                1335                1340
Val Leu Ala Thr Ala Thr Pro Pro Gly Ser Val Thr Val Pro His Pro
1345                1350                1355                136
Asn Ile Glu Glu Val Ala Leu Ser Thr Thr Gly Glu Ile Pro Phe Tyr
                1365                1370                1375
Gly Lys Ala Ile Pro Leu Glu Val Ile Lys Gly Gly Arg His Leu Ile
            1380                1385                1390
Phe Cys His Ser Lys Lys Lys Cys Asp Glu Leu Ala Ala Lys Leu Val
        1395                1400                1405
Ala Leu Gly Ile Asn Ala Val Ala Tyr Tyr Arg Gly Leu Asp Val Ser
    1410                1415                1420
Val Ile Pro Thr Ser Gly Asp Val Val Val Ala Thr Asp Ala Leu
1425                1430                1435                144
Met Thr Gly Tyr Thr Gly Asp Phe Asp Ser Val Ile Asp Cys Asn Thr
                1445                1450                1455
Cys Val Thr Gln Thr Val Asp Phe Ser Leu Asp Pro Thr Phe Thr Ile
            1460                1465                1470
Glu Thr Ile Thr Leu Pro Gln Asp Ala Val Ser Arg Thr Gln Arg Arg
        1475                1480                1485
Gly Arg Thr Gly Arg Gly Lys Pro Gly Ile Tyr Arg Phe Val Ala Pro
    1490                1495                1500
Gly Glu Arg Pro Ser Gly Met Phe Asp Ser Ser Val Leu Cys Glu Cys
1505                1510                1515                152
Tyr Asp Ala Gly Cys Ala Trp Tyr Glu Leu Thr Pro Ala Glu Thr Thr
                1525                1530                1535
Val Arg Leu Arg Ala Tyr Met Asn Thr Pro Gly Leu Pro Val Cys Gln
            1540                1545                1550
Asp His Leu Glu Phe Trp Glu Gly Val Phe Thr Gly Leu Thr His Ile
        1555                1560                1565
Asp Ala His Phe Leu Ser Gln Thr Lys Gln Ser Gly Glu Asn Leu Pro
    1570                1575                1580
```

```
Tyr Leu Val Ala Tyr Gln Ala Thr Val Cys Ala Arg Ala Gln Ala Pro
1585                1590                1595                160

Pro Pro Ser Trp Asp Gln Met Trp Lys Cys Leu Ile Arg Leu Lys Pro
            1605                1610                1615

Thr Leu His Gly Pro Thr Pro Leu Leu Tyr Arg Leu Gly Ala Val Gln
            1620                1625                1630

Asn Glu Ile Thr Leu Thr His Pro Val Thr Lys Tyr Ile Met Thr Cys
            1635                1640                1645

Met Ser Ala Asp Leu Glu Val Val Thr Ser Thr Trp Val Leu Val Gly
1650                1655                1660

Gly Val Leu Ala Ala Leu Ala Ala Tyr Cys Leu Ser Thr Gly Cys Val
1665                1670                1675                168

Val Ile Val Gly Arg Val Val Leu Ser Gly Lys Pro Ala Ile Ile Pro
            1685                1690                1695

Asp Arg Glu Val Leu Tyr Arg Glu Phe Asp Glu Met Glu Glu Cys Ser
            1700                1705                1710

Gln His Leu Pro Tyr Ile Glu Gln Gly Met Met Leu Ala Glu Gln Phe
            1715                1720                1725

Lys Gln Lys Ala Leu Gly Leu Leu Gln Thr Ala Ser Arg Gln Ala Glu
            1730                1735                1740

Val Ile Ala Pro Ala Val Gln Thr Asn Trp Gln Lys Leu Glu Thr Phe
1745                1750                1755                176

Trp Ala Lys His Met Trp Asn Phe Ile Ser Gly Ile Gln Tyr Leu Ala
            1765                1770                1775

Gly Leu Ser Thr Leu Pro Gly Asn Pro Ala Ile Ala Ser Leu Met Ala
            1780                1785                1790

Phe Thr Ala Ala Val Thr Ser Pro Leu Thr Thr Ser Gln Thr Leu Leu
            1795                1800                1805

Phe Asn Ile Leu Gly Gly Trp Val Ala Ala Gln Leu Ala Ala Pro Gly
            1810                1815                1820

Ala Ala Thr Ala Phe Val Gly Ala Gly Leu Ala Gly Ala Ala Ile Gly
1825                1830                1835                184

Ser Val Gly Leu Gly Lys Val Leu Ile Asp Ile Leu Ala Gly Tyr Gly
            1845                1850                1855

Ala Gly Val Ala Gly Ala Leu Val Ala Phe Lys Ile Met Ser Gly Glu
            1860                1865                1870

Val Pro Ser Thr Glu Asp Leu Val Asn Leu Leu Pro Ala Ile Leu Ser
            1875                1880                1885

Pro Gly Ala Leu Val Val Gly Val Val Cys Ala Ala Ile Leu Arg Arg
            1890                1895                1900

His Val Gly Pro Gly Glu Gly Ala Val Gln Trp Met Asn Arg Leu Ile
1905                1910                1915                192

Ala Phe Ala Ser Arg Gly Asn His Val Ser Pro Thr His Tyr Val Pro
            1925                1930                1935

Glu Ser Asp Ala Ala Ala Arg Val Thr Ala Ile Leu Ser Ser Leu Thr
            1940                1945                1950

Val Thr Gln Leu Leu Arg Arg Leu His Gln Trp Ile Ser Ser Glu Cys
            1955                1960                1965

Thr Thr Pro Cys Ser Gly Ser Trp Leu Arg Asp Ile Trp Asp Trp Ile
            1970                1975                1980

Cys Glu Val Leu Ser Asp Phe Lys Thr Trp Leu Lys Ala Lys Leu Met
1985                1990                1995                200
```

-continued

Pro Gln Leu Pro Gly Ile Pro Phe Val Ser Cys Gln Arg Gly Tyr Lys
                2005                2010                2015

Gly Val Trp Arg Gly Asp Gly Ile Met His Thr Arg Cys His Cys Gly
                2020                2025                2030

Ala Glu Ile Thr Gly His Val Lys Asn Gly Thr Met Arg Ile Val Gly
                2035                2040                2045

Pro Arg Thr Cys Arg Asn Met Trp Ser Gly Thr Phe Pro Ile Asn Ala
                2050                2055                2060

Tyr Thr Thr Gly Pro Cys Thr Pro Leu Pro Ala Pro Asn Tyr Thr Phe
2065                2070                2075                208

Ala Leu Trp Arg Val Ser Ala Glu Glu Tyr Val Glu Ile Arg Gln Val
                2085                2090                2095

Gly Asp Phe His Tyr Val Thr Gly Met Thr Thr Asp Asn Leu Lys Cys
                2100                2105                2110

Pro Cys Gln Val Pro Ser Pro Glu Phe Phe Thr Glu Leu Asp Gly Val
                2115                2120                2125

Arg Leu His Arg Phe Ala Pro Pro Cys Lys Pro Leu Leu Arg Glu Glu
                2130                2135                2140

Val Ser Phe Arg Val Gly Leu His Glu Tyr Pro Val Gly Ser Gln Leu
2145                2150                2155                216

Pro Cys Glu Pro Glu Pro Asp Val Ala Val Leu Thr Ser Met Leu Thr
                2165                2170                2175

Asp Pro Ser His Ile Thr Ala Glu Ala Ala Gly Arg Arg Leu Ala Arg
                2180                2185                2190

Gly Ser Pro Pro Ser Val Ala Ser Ser Ala Ser Gln Leu Ser Ala
                2195                2200                2205

Pro Ser Leu Lys Ala Thr Cys Thr Ala Asn His Asp Ser Pro Asp Ala
                2210                2215                2220

Glu Leu Ile Glu Ala Asn Leu Leu Trp Arg Gln Glu Met Gly Gly Asn
2225                2230                2235                224

Ile Thr Arg Val Glu Ser Glu Asn Lys Val Val Ile Leu Asp Ser Phe
                2245                2250                2255

Asp Pro Leu Val Ala Glu Glu Asp Glu Arg Glu Ile Ser Val Pro Ala
                2260                2265                2270

Glu Ile Leu Arg Lys Ser Arg Arg Phe Ala Gln Ala Leu Pro Val Trp
                2275                2280                2285

Ala Arg Pro Asp Tyr Asn Pro Pro Leu Val Glu Thr Trp Lys Lys Pro
                2290                2295                2300

Asp Tyr Glu Pro Pro Val Val His Gly Cys Pro Leu Pro Pro Pro Lys
2305                2310                2315                232

Ser Pro Pro Val Pro Pro Arg Lys Lys Arg Thr Val Val Leu Thr
                2325                2330                2335

Glu Ser Thr Leu Ser Thr Ala Leu Ala Glu Leu Ala Thr Arg Ser Phe
                2340                2345                2350

Gly Ser Ser Ser Thr Ser Gly Ile Thr Gly Asp Asn Thr Thr Thr Ser
                2355                2360                2365

Ser Glu Pro Ala Pro Ser Gly Cys Pro Pro Asp Ser Asp Ala Glu Ser
                2370                2375                2380

Tyr Ser Ser Met Pro Pro Leu Glu Gly Glu Pro Gly Asp Pro Asp Leu
2385                2390                2395                240

Ser Asp Gly Ser Trp Ser Thr Val Ser Ser Glu Ala Asn Ala Glu Asp
                2405                2410                2415

Val Val Cys Cys Ser Met Ser Tyr Ser Trp Thr Gly Ala Leu Val Thr

-continued

```
                      2420                2425               2430
Pro Cys Ala Ala Glu Glu Gln Lys Leu Pro Ile Asn Ala Leu Ser Asn
            2435                2440                2445
Ser Leu Leu Arg His His Asn Leu Val Tyr Ser Thr Thr Ser Arg Ser
2450                2455                2460
Ala Cys Gln Arg Gln Lys Lys Val Thr Phe Asp Arg Leu Gln Val Leu
2465                2470                2475                248
Asp Ser His Tyr Gln Asp Val Leu Lys Glu Val Lys Ala Ala Ala Ser
            2485                2490                2495
Lys Val Lys Ala Asn Leu Leu Ser Val Glu Glu Ala Cys Ser Leu Thr
            2500                2505                2510
Pro Pro His Ser Ala Lys Ser Lys Phe Gly Tyr Gly Ala Lys Asp Val
            2515                2520                2525
Arg Cys His Ala Arg Lys Ala Val Thr His Ile Asn Ser Val Trp Lys
            2530                2535                2540
Asp Leu Leu Glu Asp Asn Val Thr Pro Ile Asp Thr Thr Ile Met Ala
2545                2550                2555                256
Lys Asn Glu Val Phe Cys Val Gln Pro Glu Lys Gly Gly Arg Lys Pro
            2565                2570                2575
Ala Arg Leu Ile Val Phe Pro Asp Leu Gly Val Arg Val Cys Glu Lys
            2580                2585                2590
Met Ala Leu Tyr Asp Val Val Thr Lys Leu Pro Leu Ala Val Met Gly
            2595                2600                2605
Ser Ser Tyr Gly Phe Gln Tyr Ser Pro Gly Gln Arg Val Glu Phe Leu
            2610                2615                2620
Val Gln Ala Trp Lys Ser Lys Lys Thr Pro Met Gly Phe Ser Tyr Asp
2625                2630                2635                264
Thr Arg Cys Phe Asp Ser Thr Val Thr Glu Ser Asp Ile Arg Thr Glu
            2645                2650                2655
Glu Ala Ile Tyr Gln Cys Cys Asp Leu Asp Pro Gln Ala Arg Val Ala
            2660                2665                2670
Ile Lys Ser Leu Thr Glu Arg Leu Tyr Val Gly Gly Pro Leu Thr Asn
            2675                2680                2685
Ser Arg Gly Glu Asn Cys Gly Tyr Arg Arg Cys Arg Ala Ser Gly Val
            2690                2695                2700
Leu Thr Thr Ser Cys Gly Asn Thr Leu Thr Cys Tyr Ile Lys Ala Arg
2705                2710                2715                272
Ala Ala Cys Arg Ala Ala Gly Leu Gln Asp Cys Thr Met Leu Val Cys
            2725                2730                2735
Gly Asp Asp Leu Val Val Ile Cys Glu Ser Ala Gly Val Gln Glu Asp
            2740                2745                2750
Ala Ala Ser Leu Arg Ala Phe Thr Glu Ala Met Thr Arg Tyr Ser Ala
            2755                2760                2765
Pro Pro Gly Asp Pro Pro Gln Pro Glu Tyr Asp Leu Glu Leu Ile Thr
            2770                2775                2780
Ser Cys Ser Ser Asn Val Ser Val Ala His Asp Gly Ala Gly Lys Arg
2785                2790                2795                280
Val Tyr Tyr Leu Thr Arg Asp Pro Thr Thr Pro Leu Ala Arg Ala Ala
            2805                2810                2815
Trp Glu Thr Ala Arg His Thr Pro Val Asn Ser Trp Leu Gly Asn Ile
            2820                2825                2830
Ile Met Phe Ala Pro Thr Leu Trp Ala Arg Met Ile Leu Met Thr His
            2835                2840                2845
```

```
Phe Phe Ser Val Leu Ile Ala Arg Asp Gln Leu Glu Gln Ala Leu Asp
    2850                2855                2860

Cys Glu Ile Tyr Gly Ala Cys Tyr Ser Ile Glu Pro Leu Asp Leu Pro
2865                2870                2875                288

Pro Ile Ile Gln Arg Leu His Gly Leu Ser Ala Phe Ser Leu His Ser
                2885                2890                2895

Tyr Ser Pro Gly Glu Ile Asn Arg Val Ala Ala Cys Leu Arg Lys Leu
            2900                2905                2910

Gly Val Pro Pro Leu Arg Ala Trp Arg His Arg Ala Arg Ser Val Arg
        2915                2920                2925

Ala Arg Leu Leu Ala Arg Gly Gly Arg Ala Ala Ile Cys Gly Lys Tyr
    2930                2935                2940

Leu Phe Asn Trp Ala Val Arg Thr Lys Leu Lys Leu Thr Pro Ile Ala
2945                2950                2955                296

Ala Ala Gly Gln Leu Asp Leu Ser Gly Trp Phe Thr Ala Gly Tyr Ser
                2965                2970                2975

Gly Gly Asp Ile Tyr His Ser Val Ser His Ala Arg Pro Arg Trp Ile
            2980                2985                2990

Trp Phe Cys Leu Leu Leu Leu Ala Ala Gly Val Gly Ile Tyr Leu Leu
        2995                3000                3005

Pro Asn Arg
    3010

(2) INFORMATION FOR SEQ ID NO:2:

(i) SEQUENCE CHARACTERISTICS:
        (A) LENGTH: 120 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Ser Thr Asn Pro Lys Pro Gln Lys Lys Asn Lys Arg Asn Thr Asn
1               5                   10                  15

Arg Arg Pro Gln Asp Val Lys Phe Pro Gly Gly Gly Gln Ile Val Gly
            20                  25                  30

Gly Val Tyr Leu Leu Pro Arg Arg Gly Pro Arg Leu Gly Val Arg Ala
        35                  40                  45

Thr Arg Lys Thr Ser Glu Arg Ser Gln Pro Arg Gly Arg Arg Gln Pro
    50                  55                  60

Ile Pro Lys Ala Arg Arg Pro Glu Gly Arg Thr Trp Ala Gln Pro Gly
65                  70                  75                  80

Tyr Pro Trp Pro Leu Tyr Gly Asn Glu Gly Cys Gly Trp Ala Gly Trp
                85                  90                  95

Leu Leu Ser Pro Arg Gly Ser Arg Pro Ser Trp Gly Pro Thr Asp Pro
            100                 105                 110

Arg Arg Arg Ser Arg Asn Leu Gly
        115                 120

(2) INFORMATION FOR SEQ ID NO:3:

(i) SEQUENCE CHARACTERISTICS:
        (A) LENGTH: 590 amino acids
        (B) TYPE: amino acid
        (C) STRANDEDNESS: single
        (D) TOPOLOGY: linear
```

(ii) MOLECULE TYPE: peptide (xi) SEQUENCE DESCRIPTION: SEQ ID NO:3:

```
Asp Lys Asn Gln Val Glu Gly Glu Val Gln Ile Val Ser Thr Ala Ala
  1               5                  10                  15

Gln Thr Phe Leu Ala Thr Cys Ile Asn Gly Val Cys Trp Thr Val Tyr
             20                  25                  30

His Gly Ala Gly Thr Arg Thr Ile Ala Ser Pro Lys Gly Pro Val Ile
         35                  40                  45

Gln Met Tyr Thr Asn Val Asp Gln Asp Leu Val Gly Trp Pro Ala Pro
     50                  55                  60

Gln Gly Ser Arg Ser Leu Thr Pro Cys Thr Cys Gly Ser Ser Asp Leu
 65                  70                  75                  80

Tyr Leu Val Thr Arg His Ala Asp Val Ile Pro Val Arg Arg Arg Gly
             85                  90                  95

Asp Ser Arg Gly Ser Leu Leu Ser Pro Arg Pro Ile Ser Tyr Leu Lys
            100                 105                 110

Gly Ser Ser Gly Gly Pro Leu Leu Cys Pro Ala Gly His Ala Val Gly
            115                 120                 125

Ile Phe Arg Ala Ala Val Cys Thr Arg Gly Val Ala Lys Ala Val Asp
            130                 135                 140

Phe Ile Pro Val Glu Asn Leu Glu Thr Thr Met Arg Ser Pro Val Phe
145                 150                 155                 160

Thr Asp Asn Ser Ser Pro Pro Val Val Pro Gln Ser Phe Gln Val Ala
                165                 170                 175

His Leu His Ala Pro Thr Gly Ser Gly Lys Ser Thr Lys Val Pro Ala
            180                 185                 190

Ala Tyr Ala Ala Gln Gly Tyr Lys Val Leu Val Leu Asn Pro Ser Val
            195                 200                 205

Ala Ala Thr Leu Gly Phe Gly Ala Tyr Met Ser Lys Ala His Gly Ile
            210                 215                 220

Asp Pro Asn Ile Arg Thr Gly Val Arg Thr Ile Thr Thr Gly Ser Pro
225                 230                 235                 240

Ile Thr Tyr Ser Thr Tyr Gly Lys Phe Leu Ala Asp Gly Gly Cys Ser
                245                 250                 255

Gly Gly Ala Tyr Asp Ile Ile Ile Cys Asp Glu Cys His Ser Thr Asp
            260                 265                 270

Ala Thr Ser Ile Leu Gly Ile Gly Thr Val Leu Asp Gln Ala Glu Thr
            275                 280                 285

Ala Gly Ala Arg Leu Val Val Leu Ala Thr Ala Thr Pro Pro Gly Ser
            290                 295                 300

Val Thr Val Pro His Pro Asn Ile Glu Glu Val Ala Leu Ser Thr Thr
305                 310                 315                 320

Gly Glu Ile Pro Phe Tyr Gly Lys Ala Ile Pro Leu Glu Val Ile Lys
                325                 330                 335

Gly Gly Arg His Leu Ile Phe Cys His Ser Lys Lys Cys Asp Glu
            340                 345                 350

Leu Ala Ala Lys Leu Val Ala Leu Gly Ile Asn Ala Val Ala Tyr Tyr
            355                 360                 365

Arg Gly Leu Asp Val Ser Val Ile Pro Thr Ser Gly Asp Val Val Val
            370                 375                 380

Val Ala Thr Asp Ala Leu Met Thr Gly Tyr Thr Gly Asp Phe Asp Ser
385                 390                 395                 400
```

```
Val Ile Asp Cys Asn Thr Cys Val Thr Gln Thr Val Asp Phe Ser Leu
                405                 410                 415

Asp Pro Thr Phe Thr Ile Glu Thr Ile Thr Leu Pro Gln Asp Ala Val
            420                 425                 430

Ser Arg Thr Gln Arg Arg Gly Arg Thr Gly Arg Gly Lys Pro Gly Ile
        435                 440                 445

Tyr Arg Phe Val Ala Pro Gly Glu Arg Pro Ser Gly Met Phe Asp Ser
    450                 455                 460

Ser Val Leu Cys Glu Cys Tyr Asp Ala Gly Cys Ala Trp Tyr Glu Leu
465                 470                 475                 480

Thr Pro Ala Glu Thr Thr Val Arg Leu Arg Ala Tyr Met Asn Thr Pro
                485                 490                 495

Gly Leu Pro Val Cys Gln Asp His Leu Glu Phe Trp Glu Gly Val Phe
            500                 505                 510

Thr Gly Leu Thr His Ile Asp Ala His Phe Leu Ser Gln Thr Lys Gln
        515                 520                 525

Ser Gly Glu Asn Leu Pro Tyr Leu Val Ala Tyr Gln Ala Thr Val Cys
    530                 535                 540

Ala Arg Ala Gln Ala Pro Pro Pro Ser Trp Asp Gln Met Trp Lys Cys
545                 550                 555                 560

Leu Ile Arg Leu Lys Pro Thr Leu His Gly Pro Thr Pro Leu Leu Tyr
                565                 570                 575

Arg Leu Gly Ala Val Gln Asn Glu Ile Thr Leu Thr His Pro
            580                 585                 590

(2) INFORMATION FOR SEQ ID NO:4:

(i) SEQUENCE CHARACTERISTICS:
        (A) LENGTH: 360 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

Val Thr Lys Tyr Ile Met Thr Cys Met Ser Ala Asp Leu Glu Val Val
1               5                   10                  15

Thr Ser Thr Trp Val Leu Val Gly Gly Val Leu Ala Ala Leu Ala Ala
                20                  25                  30

Tyr Cys Leu Ser Thr Gly Cys Val Val Ile Val Gly Arg Val Val Leu
            35                  40                  45

Ser Gly Lys Pro Ala Ile Ile Pro Asp Arg Glu Val Leu Tyr Arg Glu
50                  55                  60

Phe Asp Glu Met Glu Glu Cys Ser Gln His Leu Pro Tyr Ile Glu Gln
65                  70                  75                  80

Gly Met Met Leu Ala Glu Gln Phe Lys Gln Lys Ala Leu Gly Leu Leu
                85                  90                  95

Gln Thr Ala Ser Arg Gln Ala Glu Val Ile Ala Pro Ala Val Gln Thr
            100                 105                 110

Asn Trp Gln Lys Leu Glu Thr Phe Trp Ala Lys His Met Trp Asn Phe
        115                 120                 125

Ile Ser Gly Ile Gln Tyr Leu Ala Gly Leu Ser Thr Leu Pro Gly Asn
    130                 135                 140

Pro Ala Ile Ala Ser Leu Met Ala Phe Thr Ala Ala Val Thr Ser Pro
145                 150                 155                 160
```

```
Leu Thr Thr Ser Gln Thr Leu Leu Phe Asn Ile Leu Gly Gly Trp Val
            165                 170                 175

Ala Ala Gln Leu Ala Ala Pro Gly Ala Ala Thr Ala Phe Val Gly Ala
            180                 185                 190

Gly Leu Ala Gly Ala Ala Ile Gly Ser Val Gly Leu Gly Lys Val Leu
            195                 200                 205

Ile Asp Ile Leu Ala Gly Tyr Gly Ala Gly Val Ala Gly Ala Leu Val
            210                 215                 220

Ala Phe Lys Ile Met Ser Gly Glu Val Pro Ser Thr Glu Asp Leu Val
225                 230                 235                 240

Asn Leu Leu Pro Ala Ile Leu Ser Pro Gly Ala Leu Val Val Gly Val
                    245                 250                 255

Val Cys Ala Ala Ile Leu Arg Arg His Val Gly Pro Gly Glu Gly Ala
                    260                 265                 270

Val Gln Trp Met Asn Arg Leu Ile Ala Phe Ala Ser Arg Gly Asn His
                    275                 280                 285

Val Ser Pro Thr His Tyr Val Pro Glu Ser Asp Ala Ala Ala Arg Val
                    290                 295                 300

Thr Ala Ile Leu Ser Ser Leu Thr Val Thr Gln Leu Leu Arg Arg Leu
305                 310                 315                 320

His Gln Trp Ile Ser Ser Glu Cys Thr Thr Pro Cys Ser Gly Ser Trp
                    325                 330                 335

Leu Arg Asp Ile Trp Asp Trp Ile Cys Glu Val Leu Ser Asp Phe Lys
                    340                 345                 350

Thr Trp Leu Lys Ala Lys Leu Met
                    355                 360

(2) INFORMATION FOR SEQ ID NO:5:

(i) SEQUENCE CHARACTERISTICS:
        (A) LENGTH: 1011 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

Pro Gln Leu Pro Gly Ile Pro Phe Val Ser Cys Gln Arg Gly Tyr Lys
1               5                   10                  15

Gly Val Trp Arg Gly Asp Gly Ile Met His Thr Arg Cys His Cys Gly
                20                  25                  30

Ala Glu Ile Thr Gly His Val Lys Asn Gly Thr Met Arg Ile Val Gly
                35                  40                  45

Pro Arg Thr Cys Arg Asn Met Trp Ser Gly Thr Phe Pro Ile Asn Ala
        50                  55                  60

Tyr Thr Thr Gly Pro Cys Thr Pro Leu Pro Ala Pro Asn Tyr Thr Phe
65                  70                  75                  80

Ala Leu Trp Arg Val Ser Ala Glu Glu Tyr Val Glu Ile Arg Gln Val
                85                  90                  95

Gly Asp Phe His Tyr Val Thr Gly Met Thr Thr Asp Asn Leu Lys Cys
                100                 105                 110

Pro Cys Gln Val Pro Ser Pro Glu Phe Phe Thr Glu Leu Asp Gly Val
                115                 120                 125

Arg Leu His Arg Phe Ala Pro Pro Cys Lys Pro Leu Leu Arg Glu Glu
                130                 135                 140
```

-continued

```
Val Ser Phe Arg Val Gly Leu His Glu Tyr Pro Val Gly Ser Gln Leu
145                 150                 155                 160

Pro Cys Glu Pro Glu Pro Asp Val Ala Val Leu Thr Ser Met Leu Thr
                165                 170                 175

Asp Pro Ser His Ile Thr Ala Glu Ala Ala Gly Arg Arg Leu Ala Arg
            180                 185                 190

Gly Ser Pro Pro Ser Val Ala Ser Ser Ala Ser Gln Leu Ser Ala
            195                 200                 205

Pro Ser Leu Lys Ala Thr Cys Thr Ala Asn His Asp Ser Pro Asp Ala
    210                 215                 220

Glu Leu Ile Glu Ala Asn Leu Leu Trp Arg Gln Glu Met Gly Gly Asn
225                 230                 235                 240

Ile Thr Arg Val Glu Ser Glu Asn Lys Val Val Ile Leu Asp Ser Phe
                245                 250                 255

Asp Pro Leu Val Ala Glu Glu Asp Glu Arg Glu Ile Ser Val Pro Ala
            260                 265                 270

Glu Ile Leu Arg Lys Ser Arg Arg Phe Ala Gln Ala Leu Pro Val Trp
        275                 280                 285

Ala Arg Pro Asp Tyr Asn Pro Pro Leu Val Glu Thr Trp Lys Lys Pro
290                 295                 300

Asp Tyr Glu Pro Pro Val Val His Gly Cys Pro Leu Pro Pro Pro Lys
305                 310                 315                 320

Ser Pro Pro Val Pro Pro Arg Lys Lys Arg Thr Val Val Leu Thr
                325                 330                 335

Glu Ser Thr Leu Ser Thr Ala Leu Ala Glu Leu Ala Thr Arg Ser Phe
            340                 345                 350

Gly Ser Ser Ser Thr Ser Gly Ile Thr Gly Asp Asn Thr Thr Thr Ser
            355                 360                 365

Ser Glu Pro Ala Pro Ser Gly Cys Pro Pro Asp Ser Asp Ala Glu Ser
    370                 375                 380

Tyr Ser Ser Met Pro Pro Leu Glu Gly Glu Pro Gly Asp Pro Asp Leu
385                 390                 395                 400

Ser Asp Gly Ser Trp Ser Thr Val Ser Ser Glu Ala Asn Ala Glu Asp
                405                 410                 415

Val Val Cys Cys Ser Met Ser Tyr Ser Trp Thr Gly Ala Leu Val Thr
            420                 425                 430

Pro Cys Ala Ala Glu Glu Gln Lys Leu Pro Ile Asn Ala Leu Ser Asn
    435                 440                 445

Ser Leu Leu Arg His His Asn Leu Val Tyr Ser Thr Thr Ser Arg Ser
450                 455                 460

Ala Cys Gln Arg Gln Lys Lys Val Thr Phe Asp Arg Leu Gln Val Leu
465                 470                 475                 480

Asp Ser His Tyr Gln Asp Val Leu Lys Glu Val Lys Ala Ala Ser
            485                 490                 495

Lys Val Lys Ala Asn Leu Leu Ser Val Glu Glu Ala Cys Ser Leu Thr
            500                 505                 510

Pro Pro His Ser Ala Lys Ser Lys Phe Gly Tyr Gly Ala Lys Asp Val
    515                 520                 525

Arg Cys His Ala Arg Lys Ala Val Thr His Ile Asn Ser Val Trp Lys
    530                 535                 540

Asp Leu Leu Glu Asp Asn Val Thr Pro Ile Asp Thr Thr Ile Met Ala
545                 550                 555                 560
```

-continued

```
Lys Asn Glu Val Phe Cys Val Gln Pro Glu Lys Gly Gly Arg Lys Pro
                565                 570                 575
Ala Arg Leu Ile Val Phe Pro Asp Leu Gly Val Arg Val Cys Glu Lys
            580                 585                 590
Met Ala Leu Tyr Asp Val Val Thr Lys Leu Pro Leu Ala Val Met Gly
        595                 600                 605
Ser Ser Tyr Gly Phe Gln Tyr Ser Pro Gly Gln Arg Val Glu Phe Leu
    610                 615                 620
Val Gln Ala Trp Lys Ser Lys Lys Thr Pro Met Gly Phe Ser Tyr Asp
625                 630                 635                 640
Thr Arg Cys Phe Asp Ser Thr Val Thr Glu Ser Asp Ile Arg Thr Glu
                645                 650                 655
Glu Ala Ile Tyr Gln Cys Cys Asp Leu Asp Pro Gln Ala Arg Val Ala
            660                 665                 670
Ile Lys Ser Leu Thr Glu Arg Leu Tyr Val Gly Gly Pro Leu Thr Asn
        675                 680                 685
Ser Arg Gly Glu Asn Cys Gly Tyr Arg Arg Cys Arg Ala Ser Gly Val
    690                 695                 700
Leu Thr Thr Ser Cys Gly Asn Thr Leu Thr Cys Tyr Ile Lys Ala Arg
705                 710                 715                 720
Ala Ala Cys Arg Ala Ala Gly Leu Gln Asp Cys Thr Met Leu Val Cys
                725                 730                 735
Gly Asp Asp Leu Val Val Ile Cys Glu Ser Ala Gly Val Gln Glu Asp
            740                 745                 750
Ala Ala Ser Leu Arg Ala Phe Thr Glu Ala Met Thr Arg Tyr Ser Ala
        755                 760                 765
Pro Pro Gly Asp Pro Pro Gln Pro Glu Tyr Asp Leu Glu Leu Ile Thr
    770                 775                 780
Ser Cys Ser Ser Asn Val Ser Val Ala His Asp Gly Ala Gly Lys Arg
785                 790                 795                 800
Val Tyr Tyr Leu Thr Arg Asp Pro Thr Thr Pro Leu Ala Arg Ala Ala
                805                 810                 815
Trp Glu Thr Ala Arg His Thr Pro Val Asn Ser Trp Leu Gly Asn Ile
            820                 825                 830
Ile Met Phe Ala Pro Thr Leu Trp Ala Arg Met Ile Leu Met Thr His
        835                 840                 845
Phe Phe Ser Val Leu Ile Ala Arg Asp Gln Leu Glu Gln Ala Leu Asp
    850                 855                 860
Cys Glu Ile Tyr Gly Ala Cys Tyr Ser Ile Glu Pro Leu Asp Leu Pro
865                 870                 875                 880
Pro Ile Ile Gln Arg Leu His Gly Leu Ser Ala Phe Ser Leu His Ser
                885                 890                 895
Tyr Ser Pro Gly Glu Ile Asn Arg Val Ala Ala Cys Leu Arg Lys Leu
            900                 905                 910
Gly Val Pro Pro Leu Arg Ala Trp Arg His Arg Ala Arg Ser Val Arg
        915                 920                 925
Ala Arg Leu Leu Ala Arg Gly Gly Arg Ala Ala Ile Cys Gly Lys Tyr
    930                 935                 940
Leu Phe Asn Trp Ala Val Arg Thr Lys Leu Lys Leu Thr Pro Ile Ala
945                 950                 955                 960
Ala Ala Gly Gln Leu Asp Leu Ser Gly Trp Phe Thr Ala Gly Tyr Ser
                965                 970                 975
Gly Gly Asp Ile Tyr His Ser Val Ser His Ala Arg Pro Arg Trp Ile
```

```
                       980               985                990
Trp Phe Cys Leu Leu Leu Ala Ala Gly Val Gly Ile Tyr Leu Leu
        995                1000               1005

Pro Asn Arg
    1010
```

(2) INFORMATION FOR SEQ ID NO:6:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Thr Arg Lys Thr Ser Glu Arg Ser Gln Pro Arg Gly Arg Gln Pro
1               5                   10                  15

Ile Pro Lys Ala
            20
```

(2) INFORMATION FOR SEQ ID NO:7:

(i) SEQUENCE CHARACTERISTICS:
        (A) LENGTH: 266 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Val Asp Phe Ile Pro Val Glu Asn Leu Glu Thr Thr Met Arg Ser
1                   5                   10                  15

Pro Val Phe Thr Asp Asn Ser Ser Pro Val Val Pro Gln Ser Phe
            20                  25                  30

Gln Val Ala His Leu His Ala Pro Thr Gly Ser Gly Lys Ser Thr Lys
            35                  40                  45

Val Pro Ala Ala Tyr Ala Ala Gln Gly Tyr Lys Val Leu Val Leu Asn
    50                  55                  60

Pro Ser Val Ala Ala Thr Leu Gly Phe Gly Ala Tyr Met Ser Lys Ala
65                  70                  75                  80

His Gly Ile Asp Pro Asn Ile Arg Thr Gly Val Arg Thr Ile Thr Thr
                85                  90                  95

Gly Ser Pro Ile Thr Tyr Ser Thr Tyr Gly Lys Phe Leu Ala Asp Gly
            100                 105                 110

Gly Cys Ser Gly Gly Ala Tyr Asp Ile Ile Ile Cys Asp Glu Cys His
            115                 120                 125

Ser Thr Asp Ala Thr Ser Ile Leu Gly Ile Gly Thr Val Leu Asp Gln
130                 135                 140

Ala Glu Thr Ala Gly Ala Arg Leu Val Val Leu Ala Thr Ala Thr Pro
145                 150                 155                 160

Pro Gly Ser Val Thr Val Pro His Pro Asn Ile Glu Glu Val Ala Leu
                165                 170                 175

Ser Thr Thr Gly Glu Ile Pro Phe Tyr Gly Lys Ala Ile Pro Leu Glu
            180                 185                 190

Val Ile Lys Gly Gly Arg His Leu Ile Phe Cys His Ser Lys Lys Lys
            195                 200                 205
```

```
Cys Asp Glu Leu Ala Ala Lys Leu Val Ala Leu Gly Ile Asn Ala Val
    210                 215                 220

Ala Tyr Tyr Arg Gly Leu Asp Val Ser Val Ile Pro Thr Ser Gly Asp
225                 230                 235                 240

Val Val Val Val Ala Thr Asp Ala Leu Met Thr Gly Tyr Thr Gly Asp
                245                 250                 255

Phe Asp Ser Val Ile Asp Cys Asn Thr Cys
            260                 265
```

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

```
Asp Glu Met Glu Glu Cys Ser Gln His Leu Pro Tyr Ile Glu Gln Gly
1               5                   10                  15

Met Met Leu Ala
            20
```

(2) INFORMATION FOR SEQ ID NO:9:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:9:

```
Ile Glu Gln Gly Met Met Leu Ala Glu Gln Phe Lys Gln Lys Ala Leu
1               5                   10                  15

Gly Leu Leu Gln
            20
```

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Leu Ala Glu Gln Phe Lys Gln Lys Ala Leu Gly Leu Leu Gln Thr Ala
1               5                   10                  15

Ser Arg Gln Ala
            20
```

(2) INFORMATION FOR SEQ ID NO:11:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE: peptide

```
        (xi) SEQUENCE DESCRIPTION: SEQ ID NO:11:

Val Trp Ala Arg Pro Asp Tyr Asn Pro Pro Leu Val Glu Thr Trp Lys
  1               5                  10                  15

Lys Pro Asp Tyr
            20

(2) INFORMATION FOR SEQ ID NO:12:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:12:

Glu Thr Trp Lys Lys Pro Asp Tyr Glu Pro Pro Val Val His Gly Cys
  1               5                  10                  15

Pro Leu Pro Pro
            20

(2) INFORMATION FOR SEQ ID NO:13:

(i) SEQUENCE CHARACTERISTICS:
              (A) LENGTH: 20 amino acids
              (B) TYPE: amino acid
              (C) STRANDEDNESS: single
              (D) TOPOLOGY: linear (ii) MOLECULE TYPE: peptide (xi) SEQUENCE DESCRIPTION: SEQ ID NO:13:

Val His Gly Cys Pro Leu Pro Pro Pro Lys Ser Pro Pro Val Pro Pro
  1               5                  10                  15

Pro Arg Lys Lys
            20
```